United States Patent
Ternes et al.

(10) Patent No.: US 11,202,601 B2
(45) Date of Patent: Dec. 21, 2021

(54) METHODS AND APPARATUS FOR MONITORING EPILEPSY

(71) Applicant: Cardiac Pacemakers, Inc., St. Paul, MN (US)

(72) Inventors: David J. Ternes, Roseville, MN (US); Pramodsingh Hirasingh Thakur, Woodbury, MN (US); Qi An, Blaine, MN (US); Amy Jean Brisben, Saint Paul, MN (US); Stephen B. Ruble, Lino Lakes, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 510 days.

(21) Appl. No.: 15/824,894

(22) Filed: Nov. 28, 2017

(65) Prior Publication Data

US 2018/0153460 A1    Jun. 7, 2018

Related U.S. Application Data

(60) Provisional application No. 62/428,632, filed on Dec. 1, 2016.

(51) Int. Cl.
 *A61B 5/00*     (2006.01)
 *A61B 5/30*     (2021.01)
 (Continued)

(52) U.S. Cl.
 CPC ............. *A61B 5/4094* (2013.01); *A61B 5/30* (2021.01); *A61B 5/318* (2021.01); *A61B 5/0006* (2013.01);
 (Continued)

(58) Field of Classification Search
 CPC . A61B 5/4094; A61B 5/0402; A61B 5/04004; A61B 5/0006; A61N 1/36592;
 (Continued)

(56) References Cited

U.S. PATENT DOCUMENTS

| 7,650,184 B2 | 1/2010 | Walter |
| 8,019,439 B2 | 9/2011 | Kuzma et al. |

(Continued)

FOREIGN PATENT DOCUMENTS

| WO | WO-2016110804 A1 | 7/2016 |
| WO | WO-2016123619 A1 | 8/2016 |

OTHER PUBLICATIONS

Devinsky, Orrin, "Effects of Seizures on Autonomic and Cardiovascular Function", Epilepsy Currents, vol. 4, No. 2 (Mar./Apr. 2004, pp. 43-46.

(Continued)

*Primary Examiner* — Amanda K Hulbert
*Assistant Examiner* — Natasha Patel
(74) *Attorney, Agent, or Firm* — Schwegman Lundberg & Woessner, P.A.

(57) ABSTRACT

This document discusses, among other things, systems and methods for monitoring a patient at risk of epilepsy. A system comprises a sensor circuit that senses from the patient at least first and second physiological or functional signals. A wellness detector circuit can detect an epileptic event using the sensed physiological or functional signals, or additionally classify the epileptic event into one of epileptic seizure types. The system can generate a wellness indicator based on a trend of the physiological or functional signal during the detected epileptic event. The wellness indicator indicates an impact of the detected epileptic event on the health status of the patient. The system includes an output (Continued)

unit configured to output the detection of the epileptic event or the wellness indicator to a user or a process.

20 Claims, 5 Drawing Sheets

(51) Int. Cl.
*A61B 5/318* (2021.01)
*A61N 1/36* (2006.01)
*A61N 1/365* (2006.01)
*A61N 1/362* (2006.01)

(52) U.S. Cl.
CPC .......... *A61N 1/3621* (2013.01); *A61N 1/3655* (2013.01); *A61N 1/36064* (2013.01); *A61N 1/36135* (2013.01); *A61N 1/36146* (2013.01); *A61N 1/36535* (2013.01); *A61N 1/36564* (2013.01); *A61N 1/36578* (2013.01); *A61N 1/36585* (2013.01); *A61N 1/36592* (2013.01)

(58) Field of Classification Search
CPC ............ A61N 1/36585; A61N 1/36564; A61N 1/3655; A61N 1/36535; A61N 1/3621; A61N 1/36578; A61N 1/36064; A61N 1/36135; A61N 1/36146
See application file for complete search history.

(56) References Cited

U.S. PATENT DOCUMENTS

| | | | |
|---|---|---|---|
| 9,044,188 B2 | 6/2015 | DiLorenzo et al. | |
| 2004/0167416 A1* | 8/2004 | Lee | A61B 5/0031 600/513 |
| 2007/0150025 A1* | 6/2007 | Dilorenzo | A61B 5/0476 607/45 |
| 2012/0310050 A1* | 12/2012 | Osorio | A61B 5/4094 600/300 |
| 2016/0135706 A1* | 5/2016 | Sullivan | A61B 5/0059 600/301 |

OTHER PUBLICATIONS

Ramgopal, Sriram, et al., "Seizure detection, seizure prediction, and closed-loop warning systems in epilepsy", Epilepsy & Behavior 37 (2014) 291-307.

Van De Vel, Anouk, et al., "Non-EEG seizure detection systems and potential SUDEP prevention: State of the art", Seizure 41 (2016) 141-153.

* cited by examiner

METHODS AND APPARATUS FOR MONITORING EPILEPSY

CLAIM OF PRIORITY

This application claims the benefit of priority under 35 U.S.C. § 119(e) of U.S. Provisional Patent Application Ser. No. 62/428,632, filed on Dec. 1, 2016, which is herein incorporated by reference in its entirety.

TECHNICAL FIELD

This document relates generally to medical devices, and more particularly, to systems, devices and methods for detecting and monitoring epilepsy.

BACKGROUND

Epilepsy, also known as epileptic seizure, is a group of neurological diseases that affects approximately 6.6 per 1000 people. Epilepsy can vary from brief and nearly undetectable to long periods of vigorous involuntary body movements. It represents 1-2% of all Emergency Department visits per year. Although many cases of epilepsy have unknown causes, some epileptic episodes are developed as the result of brain injury, stroke, brain tumors, infections of the brain, or birth defects. Excessive and abnormal nerve cell activity in the cortex of the brain are believed to be related to epilepsy. Some epilepsy patients have elevated risk of death. Sudden unexpected death in epilepsy (SUDEP) impairs the cardiac, respiratory and other autonomic nervous system of the patient through pathophysiological mechanisms, and accounts for about 15% of epilepsy-related deaths.

Epilepsy is typically detected made based on observation of the seizure onset and the underlying cause, and confirmed with an electroencephalogram (EEG) test. Treatment of epilepsy may include medications such as anticonvulsant drugs. However, about 40% epilepsy patients are medication resistant. Medication may also pose common side effects, including imbalance, drowsiness, upset stomach or discomfort, dizziness, or blurred vision.

Ambulatory medical devices have been used for monitoring patient health condition or disease states and delivering therapies. For example, implantable cardiac devices have been used to monitor cardiac rhythms or evaluate cardiac functions in patients with sudden cardiac death risks or having chronic heart failure. Wearable devices or stationary devices situated in a patient environment have been used for managing seizures or other neurological diseases. These devices may allow others (e.g., family members) to quickly recognize onset of an epilepsy as it develops.

SUMMARY

Epileptic seizures may affect all aspects of autonomic function, including the parasympathetic, sympathetic, and adrenal medullary systems. Seizures typically activate sympathetic nervous activity, although parasympathetic activation or sympathetic inhibition may predominate during partial seizures. Along with the autonomic function changes, cardiovascular, hemodynamic, or pulmonary functions may also vary prior to and during an epileptic seizure. For example, seizure-induced sympathetic predominance may increase the heart rate and blood pressure, disturb cardiac electrical conduction and trigger various arrhythmias (e.g., sinus tachycardia, ictal tachycardia, atrioventricular block, atrial fibrillation, supraventricular tachycardia, ventricular premature depolarizations, and bundle-branch block), and cause various respiratory symptoms (e.g., shortness of breath, tachypnea, hypopnea, apnea, reflexes such as coughing and secretions). Seizure-induced cardiovascular dysfunction, pulmonary edema, and postictal depression of autonomic respiratory reflexes and cardiovascular function may contribute to the SUDEP.

The ability to rapidly and accurately detect epileptic seizures could promote therapies aimed at rapidly treating seizures or prevent further injuries. The capability to detect seizures early and anticipate their onset prior to presentation would provide even greater advantages. These early detection and prediction systems might be able to abort seizures through targeted therapies, prevent or reduce epilepsy-related deaths such as SUDEP, and prevent accidents and limit injuries.

The stationary or wearable devices, such as smart watches or fitness devices, monitor epilepsy by recognizing a pattern of repeated body or limb movements. These devices may be well suited for convulsive seizures (e.g., tonic-clonic seizure, or other types of generalized seizure) with moderate to vigorous body or limb movements. However, approximately 40% of epileptic seizures are non-convulsive (e.g., absence seizure), typically characterized by decreased level of consciousness yet without noticeable body or limb movements. The epilepsy monitoring devices that are designed to detect vigorous movements therefore cannot adequately detect non-convulsive seizures. Additionally, these monitoring devices may not be sensitive enough to detect certain types of convulsive seizures with limited uncontrollable body or limb movements either, such as partial seizure that often presents as perceptual disturbances including sensory (visual, hearing, or smell), psychic, or autonomic disorders. Moreover, current epilepsy monitoring devices known in the art have limited capability in gathering sufficient information regarding frequency, duration and severity of patient epileptic events. Impact of epileptic seizures on a patient respiration and cardiac activity is unknown for a subject unless the seizure happens to occur in office while the subject is being monitored. As most epileptic events are ambulatory and unpredictable, such information acquired are biased due to need for self-reporting or reliance on caregiver observations. For at least these reasons, the present inventors have recognized, among other things, substantial challenges and a demand for improved system and ambulatory devices to early detection or prevention of epilepsy.

This document discusses, among other things, systems, devices, and methods for monitoring a patient at risk of epilepsy. A system may comprise a sensor circuit that may sense from the patient at least first and second physiological or functional signals. A wellness detector circuit can detect an epileptic event using the sensed first and second physiological or functional signals, or additionally classify the epileptic event into one of epileptic seizure types. A wellness indicator may be generated based on a trend of the physiological or functional signal during the detected epileptic event. The wellness indicator indicates an impact of the detected epileptic event on the health status of the patient. The system includes an output unit configured to output the detection of the epileptic event or the wellness indicator to a user or a process. The system may monitor a patient for epileptic event without requiring acquisition or processing of a brain signal such as an electroencephalogram.

Example 1 is a system for monitoring a patient at risk of epilepsy. The system comprises a sensor circuit, a wellness detector circuit, and an output circuit. The sensor circuit may be coupled to a first sensor to sense from the patient a first physiological or functional signal and a second sensor to sense from the patient a different second physiological or functional signal. The wellness detector circuit may be communicatively coupled to the sensor circuit, and configured to detect an epileptic event using the sensed first and second physiological or functional signals, and generate a wellness indicator based on a trend of the first or second physiological or functional signal over time during the detected epileptic event. The wellness indicator indicates an impact of the detected epileptic event on the health status of the patient. The output unit may be configured to output the detection of the epileptic event or the wellness indicator to a user or a process.

In Example 2, the subject matter of Example 1 optionally includes a memory configured to store the sensed first and second physiological or functional signals in response to the detection of the epileptic event.

In Example 3, the subject matter of any one or more of Examples 1-2 optionally includes the wellness indicator that may include a risk of sudden unexpected death in epilepsy.

In Example 4, the subject matter of any one or more of Examples 1-3 optionally includes the wellness indicator that may include one or more of: a degree of progression of a chronic disease; a risk of cardiac arrhythmia; a risk of a syncope; a risk of pulmonary edema; or a risk of disordered breathing pattern.

In Example 5, the subject matter of any one or more of Examples 1-4 optionally includes the sensor circuit which may be coupled to the first or second sensor to detect a physiological signal including one or more of: a heart rate signal; a heart rate variability signal; a respiration rate signal; a blood pressure signal; a blood pressure variability signal; a peripheral body temperature signal; or a heart sound signal.

In Example 6, the subject matter of any one or more of Examples 1-5 optionally includes the sensor circuit which may be coupled to the first or second sensor configured to sense a functional signal including one or more of: a posture; a physical activity intensity or duration; a grip strength signal; a gait; or a balance indicator.

In Example 7, the subject matter of any one or more of Examples 1-6 optionally includes the wellness detector circuit which may be configured to detect the epileptic event using the first and second physiological or functional signals respectively weighted by weight factors indicating respective physiological or functional signal reliability in evaluating a patient risk of developing an epileptic episode.

In Example 8, the subject matter of any one or more of Examples 1-7 optionally includes the wellness detector circuit that may further be configured to: generate, from the sensed first and second physiological or functional signals, one or more epileptic characteristics including an intensity, a duration, or a frequency of detected epileptic event; and classify the detected epileptic event into one of a plurality of epilepsy types using the one or more epileptic characteristics.

In Example 9, the subject matter of Example 8 optionally includes the wellness detector circuit that may be configured to classify the detected epileptic event into an epileptic seizure type including one or more of: a general seizure; a partial seizure; a tonic seizure; an atonic seizure; or a clonic seizure.

In Example 10, the subject matter of any one or more of Examples 1-9 optionally includes the sensor circuit that may be configured to sense the first and second physiological or functional signal at a peri-epilepsy sampling rate higher than a pre-epilepsy sampling rate in response to the detection of the epileptic event.

In Example 11, the subject matter of any one or more of Examples 1-10 optionally includes an ambulatory medical device (AMD) communicatively coupled to the first and second sensors. The AMD may include at least a portion of one or more of the sensor circuit, the wellness detector circuit, and the output unit.

In Example 12, the subject matter of Example 11 optionally includes an external system in communication with the AMD. The external system may include an external data processor configured to confirm the detection of the epileptic event.

In Example 13, the subject matter of Example 12 optionally includes the AMD that may further include a telemetry circuit configured to transmit the first and second physiological or functional signals to the external system periodically or upon a receipt of a command.

The external data processor may be configured to confirm the detection of the epileptic event using the transmitted first and second signals.

In Example 14, the subject matter of any one or more of Examples 1-13 optionally includes a therapy unit configured to deliver a neural or cardiac electrostimulation therapy in response to the detection of an epileptic event.

In Example 15, the subject matter of Example 14 optionally includes the therapy unit that may be configured to deliver the neural or cardiac electrostimulation therapy further in accordance with one or more epileptic characteristics or a classification of the epileptic event into one of a plurality of epileptic seizure types.

Example 16 is a method for detecting epilepsy in a patient with an ambulatory device. The method comprises steps of: sensing, via the ambulatory device, first and different second physiological or functional signals; detecting an epileptic event using the sensed first and second physiological or functional signals; generating a wellness indicator based on a trend of the first or second physiological or functional signal over time during the detected epileptic event, the wellness indicator indicating an impact of the detected epileptic event on the health status of the patient; and outputting the detection of the epileptic event or the wellness indicator to a user or a process.

In Example 17, the subject matter of Example 16 optionally includes the wellness indicator that may include one or more of: a degree of progression of a chronic disease; a risk of sudden unexpected death in epilepsy; a risk of cardiac arrhythmia; a risk of a syncope; a risk of pulmonary edema; or a risk of disordered breathing pattern.

In Example 18, the subject matter of any one or more of Examples 16-17 optionally includes the step of detecting the epileptic event that may include linearly or nonlinearly combining the first and second physiological or functional signals respectively weighted by weight factors indicating respective physiological or functional signal reliability in evaluating a patient risk of developing an epileptic episode.

In Example 19, the subject matter of any one or more of Examples 16-18 optionally includes steps of: generating, from the sensed first and second physiological or functional signals, one or more epileptic characteristics including an intensity, a duration, or a frequency of detected epileptic event; and classifying the detected epileptic event into one of a plurality of epilepsy types using the one or more epileptic characteristics.

In Example 20, the subject matter of any one or more of Examples 16-19 optionally includes the step of sensing the first and second physiological or functional signal which may include sensing the first and second physiological or functional signal at a peri-epilepsy sampling rate higher than a pre-epilepsy sampling rate in response to the detection of the epileptic event.

In Example 21, the subject matter of any one or more of Examples 16-20 optionally includes steps of transmitting the first and second physiological or functional signals to an external system, and confirming the detection of the epileptic event at an external system using the first and second physiological or functional signals.

In Example 22, the subject matter of any one or more of Examples 16-21 optionally include a step of delivering a neural or cardiac electrostimulation therapy in response to the detection of an epileptic event.

In Example 23, the subject matter of Example 22 optionally includes delivering the neural or cardiac electrostimulation therapy further in accordance with one or more epileptic characteristics or a classification of the epileptic event into one of a plurality of epileptic seizure types.

In Example 24, a system may optionally combine any portion or combination of any portion of any one or more of Examples 1-23 to include "means for" performing any portion of any one or more of the functions or methods of Examples 1-23, or a "non-transitory machine-readable medium" including instructions that, when performed by a machine, cause the machine to perform any portion of any one or more of the functions or methods of Examples 1-23.

Monitoring epilepsy and assessing patient wellness during an epileptic event using physiological sensors as discussed in this document, may improve medical diagnostics of epileptic events, as well as individualized therapies to improve patient outcome. The systems, devices, and methods discussed in this document may also enhance the performance and functionality of an epilepsy management system or device. A device or a system programmed with the sensor-based epilepsy detection methods can have improved automaticity in medical diagnostics. More efficient device memory or communication bandwidth usage may be achieved by storing or transmitting medical information more relevant to clinical decisions. Additionally, through epileptic therapies based on patient individual need and therapy efficacy, battery longevity of an implantable device may be enhanced, or antiepileptic medication volume may be saved.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for monitoring a patient at risk of epilepsy. Physiological or functional signals may be sensed from the patient, which are used to detect presence of an epileptic event. A wellness that indicates an impact of the detected epileptic event on the health status of the patient may be generated. Healthcare professionals may be alerted about the detection of the epileptic event, or the detected epileptic event satisfying a specific condition such as surpassing a threshold value for a duration or other measure of severity that impact the patient cardiac or respiratory function. A therapy may be delivered to treat or control the epileptic event based on the detection of the epileptic event, or when the detected epileptic event satisfies the specific condition.

Figure 1:
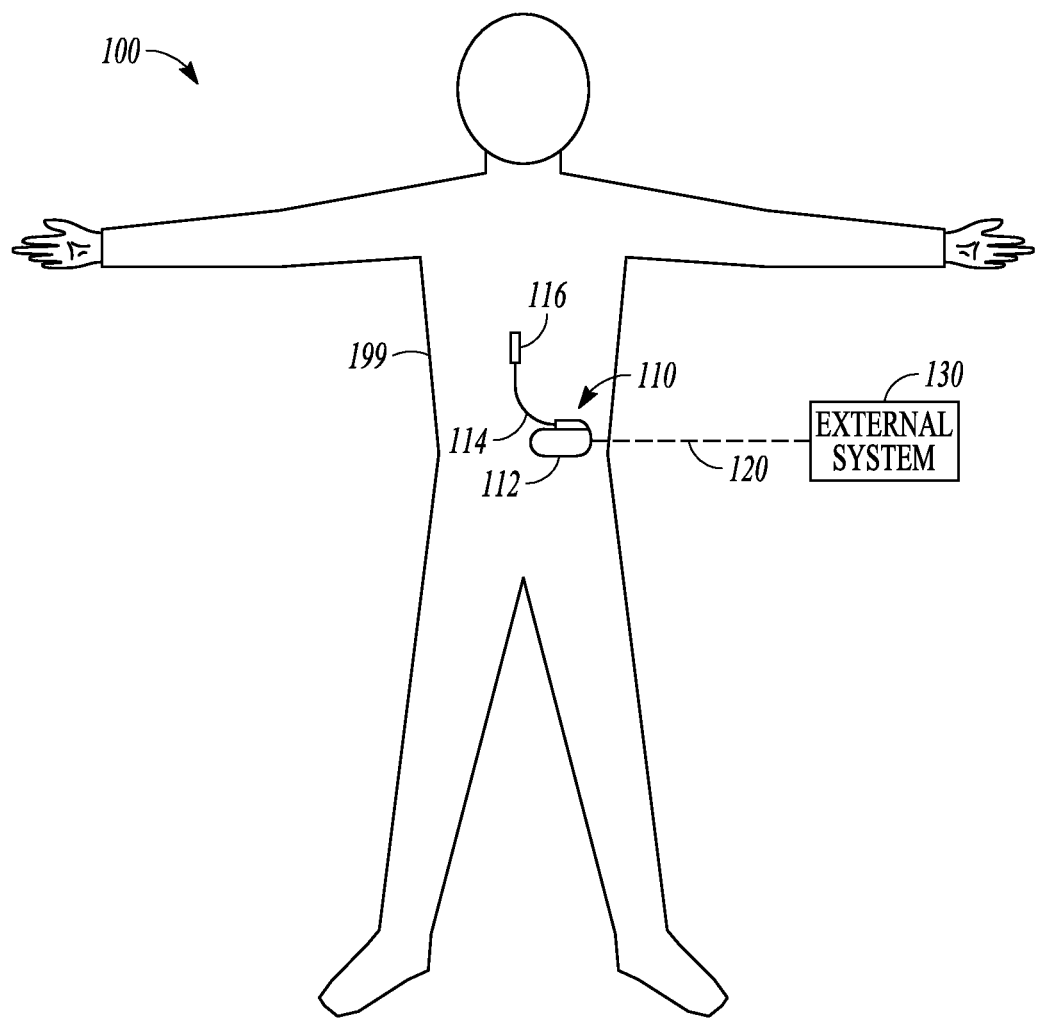
FIG. 1 illustrates generally an example of an epilepsy management system and portions of an environment in which the epilepsy management system may operate.

FIG. 1 illustrates generally an example of an epilepsy management system 100 and portions of an environment in which the epilepsy management system 100 may operate. The epilepsy management system 100 may include an ambulatory system 110 that may be associated with a body of a patient 199, and an external system 130. A communication link 120 is provided by communication between the ambulatory system 110 and the external system 130.

The ambulatory system 110 may include an implantable medical device (IMD) 112, a lead system 114, and one or more electrodes 116. The IMD 112 may be subcutaneously implanted in chest, abdomen, or other parts of the body of the patient 199. Alternatively, the IMD 112 may be implanted under the skull. In an example, the IMD 112 may be configured as a monitoring and diagnostic device. The IMD 112 may sense physiological and functional signals in the patient, and predict an impending epileptic event (e.g., by detecting early indications or signs of epilepsy) or detect an onset of epileptic event. Upon an early detection or prediction of epileptic event, the IMD 112 may additionally perform peri-epileptic or post-epileptic monitoring of a patient cardiac, hemodynamic, respiratory, or neural activity. In another example, the IMD 112 may be configured as a therapeutic device which, in addition to patient monitoring and epilepsy diagnosis, may generate and deliver a therapy to the patient to prevent occurrence of an epileptic seizure, or to treat or control epilepsy and complications, such as by modifying, restoring, or improving patient neural, cardiac, or respiratory functions. Examples of the therapy may include electrical, magnetic, or other forms of therapy. In some examples, the IMD 112 may include a drug delivery system such as a drug infusion pump device to deliver drug therapy to the patient to manage epilepsy.

The IMD 112 may include a hermetically sealed can that houses circuitries to achieve different functions. Depending on the configuration of the IMD 112 as either a monitoring device or a therapeutic device, the IMD 112 may house one or more of sensing circuitry, electrostimulation circuitry, control circuitry, communication circuitry, a battery, among other components. The sensing circuitry of the IMD 112 may be configured to sense physiological or functional signals in the patient via sensing electrodes or ambulatory sensors associated with the patient. The physiological or functional signals may contain information about changes in a patient cardiovascular, pulmonary, or neurological responses prior to and during the development of an epileptic event. The physiological or functional signals may additionally contain information of signs and symptoms of a patient prior to and during an epileptic event. The physiological or functional signals may include signals other than a brain signal such as an electroencephalogram signal, such that the IMD 112 may monitor a patient for epileptic event without requiring acquisition or processing of a brain signal. The IMD 112 may detect an epileptic event using the sensed physiological or functional signals, or additionally classify the epileptic event into one of epilepsy types. The IMD 112 may additionally monitor patient post-epileptic impact of short-term insult to cardiac or pulmonary system, or use the physiological or functional signals to assess efficacy of an antiepileptic therapy.

The electrostimulation circuitry may generate electrostimulation pulses to stimulate a target tissue, such as via the electrodes 116 operably connected to the IMD 112, to treat on-going epilepsy or to prevent an impending epileptic event. In an example, the electrodes 116 may be positioned on or near a spinal cord, and the electrostimulation circuitry may be configured to deliver spinal cord stimulation (SCS) to block or regulate sympathetic surge. In another example, the electrodes 116 may be surgically placed at a brain tissue, and the electrostimulation circuitry may be configured to deliver deep brain stimulation (DBS) to identified seizure foci of the brain, such as at the anterior nucleus of thalamus. In various examples, the electrodes 116 may be positioned at peripheral neutral targets such as a vagus nerve, and the electrostimulation circuitry may be configured to deliver peripheral neuromodulation such as vagus nerve stimulation (VNS). In yet another example, the electrostimulation circuitry may be configured to provide baroreceptor stimulation (BRS) via electrodes positioned at or near a baroreceptor to maintain blood pressure. In some examples, the antiepileptic therapy may be delivered in a closed-loop fashion, where one or more therapy parameters may be adjusted or drug dosage titrated according to an efficacy of the antiepileptic therapy delivered. The therapy efficacy may be assessed based on sensor feedback, such as the physiological or functional signals sensed during or after the epilepsy event.

In various examples, the electrodes 116 may be distributed in one or more leads of the lead system 114 electrically coupled to the IMD 112. The electrodes 116 may be used for sensing physiological signal or delivering electrostimulation. In an example, the lead system 114 may include a directional lead that includes at least some segmented electrodes circumferentially disposed about the directional lead. Two or more segmented electrodes may be distributed along a circumference of the lead. The actual number and shape of leads and electrodes may vary according to the intended application. Detailed description of construction and method of manufacturing percutaneous stimulation leads are disclosed in U.S. Pat. No. 8,019,439, entitled "Lead Assembly and Method of Making Same," and U.S. Pat. No. 7,650,184, entitled "Cylindrical Multi-Contact Electrode Lead for Neural Stimulation and Method of Making Same," the disclosures of which are incorporated herein by reference. The electrodes 116 may provide an electrically conductive contact providing for an electrical interface between the IMD 112 and tissue of the patient. The neurostimulation pulses are each delivered from the IMD 112 through a set of electrodes selected from the electrodes 116. In various examples, the neurostimulation pulses may include one or more individually defined pulses, and the set of electrodes may be individually definable by the user for each of the individually defined pulses.

Although the discussion herein with respect to the epilepsy management system 100 focuses on implantable system (e.g., the IMD 112), this is meant only by way of example and not limitation. It is within the contemplation of the inventors and within the scope of this document, that the systems, devices, and methods discussed herein may also be used implemented in, and executed by, a subcutaneous medical devices, wearable medical devices (e.g., watch-like devices, patch-based devices, or other accessories), or other ambulatory medical devices. Such ambulatory systems, while being used for monitoring, diagnosing, or treating epilepsy, may be modified or reconfigured for other applications such as chronic pain management, obsessive compulsive disorder, tremor, Parkinson's disease, or dystonia, among other neurological diseases.

The external system 130 may be communicated with the IMD 112 via a communication link 120. The external system 130 may include a dedicated hardware/software system such as a programmer, a remote server-based patient management system, or alternatively a system defined predominantly by software running on a standard personal computer. The external system 130 may control the operation of the IMD 112, such as to program the IMD 112 for detecting epilepsy and/or delivering an antiepileptic therapy. The external system 130 may additionally receive via the communication link 120 information acquired by IMD 112, such as one or more physiological or functional signals. The external system 130 may include a display for displaying the physiological or functional signals and the detection of epilepsy, or alerts, alarms, emergency calls, or other forms of warnings to signal the presence or types of epileptic event.

In an example, the external system 130 may include an external data processor configured to analyze the physiological or functional signals received by the IMD 112, and to confirm or reject the detection of the epileptic event.

Computationally intensive algorithms, such as machine-learning algorithms, may be implemented in and executed by the external data processor. Retrospective data analysis may be performed therein to provide an individualized prediction of an impending epileptic event, thus to allow the patient to have enough time to react (e.g., to seek immediate medical attention). Additionally, the external data processor may assess therapy efficacy based on the physiological or functional signals received from the IMD 112, and program the IMD 112 to deliver antiepileptic therapy such as in a closed-loop fashion.

The communication link 120 may include one or more communication channels and intermediate devices between the external system and the IMD 112, such as a wired link, a telecommunication link such as an internet connection, or a wireless link such as one or more of an inductive telemetry link, a radio-frequency telemetry link. The communication link 120 may provide for data transmission between the IMD 112 and the external system 130. The IMD 112 may include a telemetry circuit configured to transmit the physiological or functional signals, along with other data, to the external system 130 periodically or upon a receipt of a command. The data may be transmitted in a batch mode, in a specified transmission cycle such as every one hour, to save the power consumption and efficiently use the communication bandwidth. The transmitted data may include, for example, real-time physiological data acquired by the IMD 112, physiological data acquired by and stored in the IMD 112, therapy history data, data indicating device operational status of the IMD 112, one or more programming instructions to the IMD 112 which may include configurations for sensing physiologic signal or stimulation commands and stimulation parameters, or device self-diagnostic test, among others. In some examples, the IMD 112 may be coupled to the external system 130 further via an intermediate control device, such as a handheld external remote control device to remotely instruct the IMD 112 to generate electrical stimulation pulses in accordance with selected stimulation parameters produced by the external system 130.

Portions of the IMD 112 or the external system 130 may be implemented using hardware, software, firmware, or combinations thereof. Portions of the IMD 112 or the external system 130 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
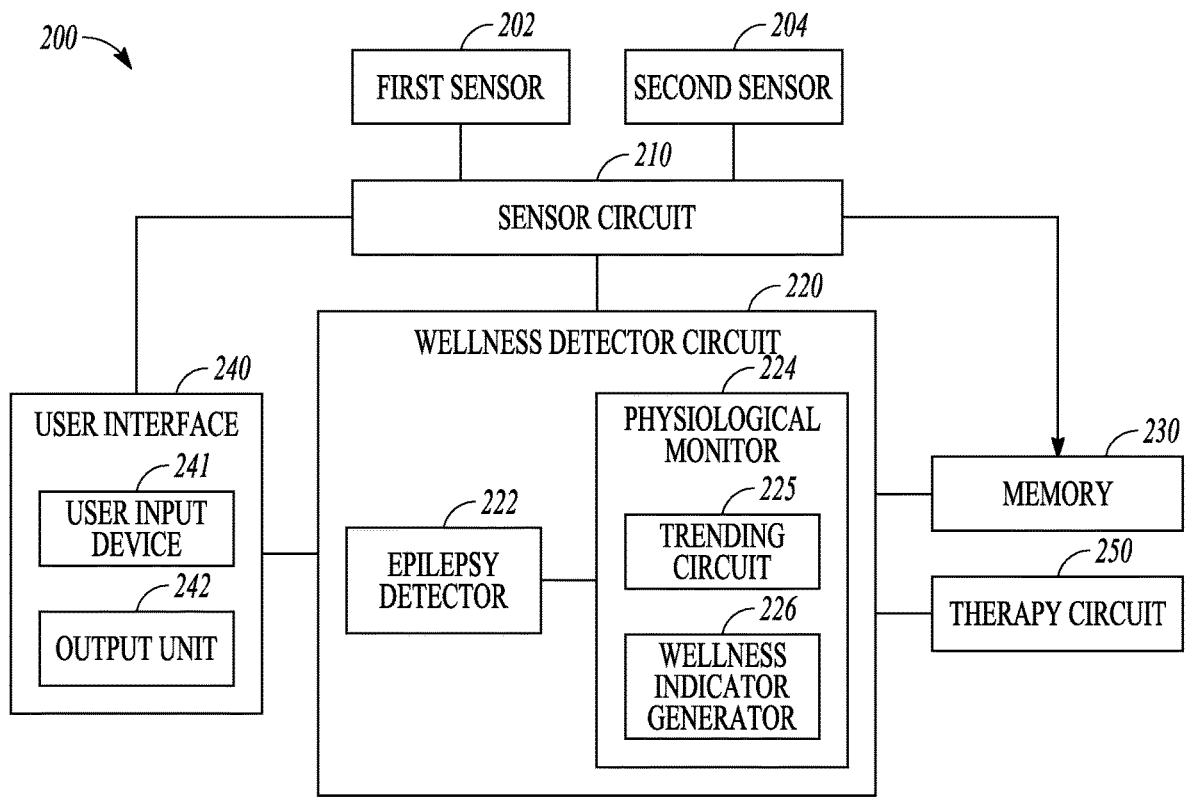
FIG. 2 illustrates generally an example of a multi-sensor epilepsy management system.

FIG. 2 illustrates generally an example of a multi-sensor epilepsy management system 200. The multi-sensor epilepsy management system 200 may include a sensor circuit 210, a wellness detector circuit 220, a memory 230, and a user interface 240. The system 200 may optionally include a therapy circuit 250. The multi-sensor epilepsy management system 200 may be an embodiment of the epilepsy management system 100. In an example, at least a portion of one or more of the sensor circuit 210, the wellness detector circuit 220, the memory 230, the user interface 240, or the optional therapy circuit 250 may be included in an ambulatory device such as the IMD 112, or distributedly implemented between an ambulatory device and an external device such as a programmer or a remote patient management system.

The sensor circuit 210 may include sense amplifiers coupled to two or more sensors, such as a first sensor 202 and a second sensor 204, to sense multiple physiological or functional signals in the patient. The physiological signals may include cardiac, pulmonary, hemodynamic, neural, or biochemical signals. Examples of the physiological signal may include electrocardiograph (ECG), an electrogram (EGM), a heart rate signal, a heart rate variability signal, an intrathoracic impedance signal, an intracardiac impedance signal, an arterial blood pressure signal, a pulmonary artery pressure signal, a RV pressure signal, a LV coronary pressure signal, a blood pressure variability signal, a coronary blood temperature signal, a peripheral body temperature signal, a blood oxygen saturation signal, a heart sound (HS) signal, or a respiration signal (including, for example, respiration rate, tidal volume, minute ventilation, respiratory patterns), a galvanic skin response (GSR) signal, or a neural signal such as indicative of sympathetic or parasympathetic tone, among others. Examples of the functional signals may include a posture, a gait, a balance indicator, a locomotion pattern, a physical activity intensity or duration, or a grip strength signal, among others.

In an example, the sensor circuit 210 may be coupled to one or more electrodes such as on the lead system 114 and the can housing of the IMD 112, or one or more implantable, wearable, or other ambulatory sensors to sense the physiological or functional signals. Examples of physiological or functional sensors may include pressure sensors, flow sensors, impedance sensors, accelerometers, microphone sensors, respiration sensors, temperature sensors, or blood chemical sensors, among others. In various examples, an accelerometer may be used to detect an activity intensity or activity duration. A tilt switch, an accelerometer, or a thoracic impedance sensor may be used to detect posture or position. Gyroscope, magnetoresistive sensors, inclinometers, goniometers, electromagnetic tracking system (ETS), sensing fabric, force sensor, strain gauges, and sensors for electromyography (EMG) may be used to measure motion and gaits. In an example, the sensor circuit 210 may be coupled to a device capable of collecting or storing the physiologic information, such as an external programmer, an electronic medical record (EMR) system, or a memory unit, among other data storage devices.

The sense amplifier circuit can pre-process the one or more physiological or functional signals, including, for example, amplification, digitization, filtering, or other signal conditioning operations. The sensor circuit 210 may generate from the preprocessed physiological or functional signals signal metrics representing physiological or functional changes in response to a patient disease progression, change in medication, change in health conditions, or change in posture or activity levels. In an example, the sensor circuit 210 may receive a transthoracic impedance signal from the electrodes on the lead system 114 and the can housing of the IMD 112, and generate a signal metric of direct-current (DC) impedance using the transthoracic impedance signal. In another example, the sensor circuit 210 may sense a HS signal from an accelerometer or an acoustic sensor coupled to the IMD 110, and generate two or more HS metrics. Examples of the HS metrics may include intensities of S1, S2, S3, or S4 heart sounds, or timing of the S1, S2, S3, or S4 heart sound with respect to a fiducial point such as a P wave, Q wave, or R wave in an ECG. In an example, the sensor circuit 210 may sense a blood pressure signal via a pressure sensor and generate two or more blood pressure signal metrics which may include systolic blood pressure, diastolic blood pressure, mean arterial pressure, and the timing metrics of these pressure measurements with respect to a fiducial point.

The wellness detector circuit 220 may include circuit sets comprising one or more other circuits or sub-circuits. The circuits or sub-circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

In various examples, the wellness detector circuit 220 may be implemented as a microprocessor circuit, such as a dedicated processor such as a digital signal processor, application specific integrated circuit (ASIC), microprocessor, or other type of processor for processing information including the physiological signals received from the sensor circuit 210. Alternatively, the microprocessor circuit may be a general purpose processor that may receive and execute a set of instructions of performing the functions, methods, or techniques described herein.

As illustrated in FIG. 2, the wellness detector circuit 220, which is communicatively coupled to the sensor circuit 210, may include an epilepsy detector 222 and a physiological monitor 224. The epilepsy detector 222 may detect an epileptic event using the sensed first and second physiological or functional signals. The epilepsy detector 222 may compare the signal metrics of the physiological or functional signals to one or more thresholds or to fit a computational model to determine the presence or absence of the epileptic event.

In an example, the epilepsy detector 222 may include a blending circuit that may generate an epilepsy indictor using a combination of signal metrics generated from the first and second physiological or functional signals. The blending circuit may employ a computation model that performs linear or nonlinear combination of signal metrics. Examples of the computation models may include a linear weighted combination, a nonlinear combination such as a decision tree, a neural network, a fuzzy-logic model, or a multivariate regression model, among others. In an example, the signal metrics may be respectively weighted by weight factors when they are combined. The weight factors indicate respective physiological or functional signal reliability in evaluating a patient risk of developing an epileptic episode. In an example, the reliability may be determined using historical data from the patient, including the physiological or functional signals acquired during epileptic events in patient medical history. A signal metric that manifests greater and more consistent changes in signal amplitude or signal power is deemed more reliable that another signal metric with smaller changes, or greater variability, in signal amplitude or signal power. A larger weight may be assigned to the more reliable signal metric than to a less reliable signal metric when establishing a linear or non-linear combination of the signal metrics. The epilepsy detector 222 may include a comparator to compare the epilepsy indicator to a predetermined condition and detect the epileptic event when the condition is satisfied. In an example, the epilepsy indicator is a numerical risk score computed as weighted sum of individual scores representing likelihood of impending epilepsy predicted by individual signal metrics. The epilepsy detector 222 may detect the epileptic event when the numerical risk score exceeds a specified risk threshold. In some examples, the epilepsy detector 222 may quantify the likelihood of an epileptic event further based upon patient prior epileptic events or other neurological disorders in patient medical history, or based on data from epilepsy patient population.

The epilepsy detector 222 may alternatively detect an epileptic event using a sequential process. Physiological and functional signals may demonstrate different time course in responding to an epilepsy event. For example, there may be early cardiac, hemodynamic, or respiratory response prior to an onset of epileptic attack, when no signs or symptomatic changes in posture, gait, physical activity, or other behavioral or functional changes appear or may be reliably detected by sensors. When taking into account such differences in temporal responses, the epilepsy detector 222 may generate an initial epilepsy indicator based on one or more physiological signal metrics, such as cardiac, hemodynamic, or respiratory signal metrics. The epilepsy detector 222 may confirm or reject the initial epilepsy indicator using functional metrics that are generated from time-lagged functional signals acquired subsequent to the physiological signals. An epileptic event is detected when the initial detection is confirmed by the analysis of the time-lagged functional signals.

The physiological monitor 224 may monitor a patient physiological status upon a prediction or early detection of the epileptic seizure and provide an assessment of the impact of epileptic seizure on the patient health. The wellness indicator generator 224 may include a trending circuit 225 and a wellness indicator generator. The trending circuit 225 may be configured to generate a first trend of the first physiological or functional signal and a second trend of the second physiological or functional signal over time. The first and second trends may be established during the detected epileptic event, or even extended after the termination of the epileptic event. The wellness indicator generator 226 may generate an indication of the impact of the detected epileptic event on patient health status. The wellness indicator may also indicate an impact on patient psychiatric health, such as fear of epilepsy recurrence and health consequences or depression, which may last for an extended period of time post an epileptic event. In an example, the wellness indicator may include an epilepsy complication risk such as a risk of sudden unexpected death in epilepsy (SUDEP). For example, it has been identified that epileptic seizures can cause short-term and long-term heart rate disturbances, which play a pivotal role in SUDEP pathophysiology. Cardiac monitoring during epilepsy may be critical preventing SUDEP or other injuries.

During seizures, respiratory and cardiac activities may be impaired such as due to catecholamine surges, autonomic dysregulation, or cerebral vascular dysregulation, among other causes. For example, prior to and during complex partial seizures or tonic-clonic seizures, discharges in the right insular cortex may disturb electrophysiological conduction system in the heart, and increase the risk for tachyarrhythmia. The first and/or second trend may include trends of cardiac and hemodynamic parameters, and the wellness indicator may indicate risks of syncope, arrhythmias such as bradycardia or tachycardia, hypotension, or blood pressure instability. The identified risk may be used to identify patients that may benefit from a particular therapy or candidate for receiving a diagnostic or therapeutic device, such as a cardiac rhythm or function management device. For patients having an implantable device, the wellness indicator generator 226 may provide assessment of an impact of the epilepsy on the functionality of an implantable device, such as arrhythmia detection or arrhythmia therapy (e.g., cardiac pacing for bradycardia, antitachycardia pacing or defibrillation shock therapy for tachycardia, or resynchronization therapy for heart failure), and provide an indication for therapy parameter adjustment, drug dosage titration, device reconfiguration, or device upgrade. In another example, the first and/or second trend may include trends of respiratory parameters (e.g., respiratory rate, tidal volume, or respiratory pattern), and the wellness indicator may indicate a risk of disordered breathing. The first and/or second trend may additionally or alternatively include trends of a thoracic impedance parameter, and the wellness indicator may indicate a risk of neurogenic pulmonary edema. Epilepsy may exacerbate the pre-existing chronic disease. The wellness indicator based on the first or second trend may indicate a degree of progression of a chronic disease such as a heart failure or a chronic obstructive pulmonary disease (COPD). For example, the wellness indicator may also indicate an improved cardiopulmonary function and reduced likelihood of future epileptic events. As the cardiopulmonary activity may perturb the autonomic nervous system and such a perturbation may trigger an epileptic event, improvement in patient cardiopulmonary health (e.g., reduction in apnea, COPD, asthma, or cardiac arrhythmias, or improved cardiac function) may lead to fewer epileptic events.

The memory 230 may be configured to store sensor signals or signal metrics such as generated by the sensor circuit 210, and the detected epileptic events and the wellness indicators during and after the epileptic events. Data storage at the memory 230 may be continuous, periodic, or triggered by a user command or a specified event. In an example, a detection of epileptic event may trigger the data storage of selected physiological or functional signals with respectively specified time duration. For example, the stored data may sustain from a specified pre-event time prior to the onset of the epilepsy detection till a specified post-event time after the termination of the epileptic event. In an example, an interrogating device, such as a programmer in the external system 130 as illustrated in FIG. 1 and a remote server-based patient management system, may request access to the stored sensor signals, the epileptic events, and the wellness indicator stored in the memory 230. Other device data, such as sensing, pacing, timestamps, or event markers as generated and stored in an implantable cardiac device, may also be requested. The requested information may be forwarded to the interrogating device such as via the communication link 120, where the information may be displayed or undergo further analysis, such as to confirm or reject the epilepsy detection or the physiological impact of the epilepsy.

The user interface 240 may include an input device 241 and an output unit 242. In an example, at least a portion of the user interface 240 may be implemented in the external system 130. The input device 241 may enable a user to provide parameters for sensing physiological or functional signals, parameters for detecting epileptic events, or parameters for trending the physiological or functional signals during and after the detected epileptic events. The input device 241 may include an input device such as a keyboard, on-screen keyboard, mouse, trackball, touchpad, touchscreen, or other pointing or navigating devices. The output unit 242 may generate a human-perceptible presentation of information including the detection of the epileptic event or the wellness indicator. The output unit 242 may include a display for displaying the information, or a printer for printing hard copies of the information. The information may be presented in a table, a chart, a diagram, or any other types of textual, tabular, or graphical presentation formats, for displaying to a system user. The presentation of the output information may include audio or other media format to inform the system user of the detected physiological events. In an example, the output unit 242 may generate alerts, alarms, emergency calls, or other forms of warnings to signal the presence or types of epileptic events, and the wellness indicator such as indicating deteriorated cardiac, hemodynamic, pulmonary, or neurological functions. In some examples, the output unit 242 may generate report to clinicians, which may include notification or recommendation in patient management such as therapy titration, including therapy type (e.g., drug therapy or device therapy), dosage or therapy parameters, timing, or duration, among other therapy information.

The optional therapy circuit 250 may be configured to deliver a therapy to the patient in response to the detection of an epileptic event. In some examples, the optional therapy circuit 250 may be configured to deliver prophylactic therapy. The wellness detector circuit 220 may monitor effectiveness in suppressing epileptic events, such as a reduction in number, duration, or severity of epileptic events. Examples of the therapy may include electrostimulation therapy delivered to a neural target to treat epileptic seizure. Examples of such antiepileptic therapy may include SCS, DBS, or VNS. In some examples, the therapy circuit 250 may control a drug infusion pump to deliver antiepileptic medications. In some examples, the therapy may be delivered in a closed-loop fashion. The therapy efficacy may be assessed based on sensor feedback, such as the physiological or functional signals sensed during or after the epilepsy event. One or more therapy parameters may be adjusted, or a dosage of a drug therapy may be tailored, in accordance with the efficacy of antiepileptic therapy delivered.

In addition to the antiepileptic therapy, the therapy circuit 250 may provide assistive therapies to maintain adequate cardiorespiratory and hemodynamic support during and after epilepsy treatment. The assistive therapies may include respiratory rate regulation, heart rate regulation, cardiac pacing for bradycardia support, pacing or cardioversion or high energy shock therapies for tachycardia support, cardiac synchronization therapy to restore systolic function, or baroreceptor stimulation via electrodes positioned at or near a baroreceptor to maintain blood pressure and adequate hemodynamic support, among others. The peri- and post-epileptic assistive therapy may be sustained until a patient physiologic response adequately recovers, such as to a level comparable to a pre-epileptic baseline.

Figure 3:
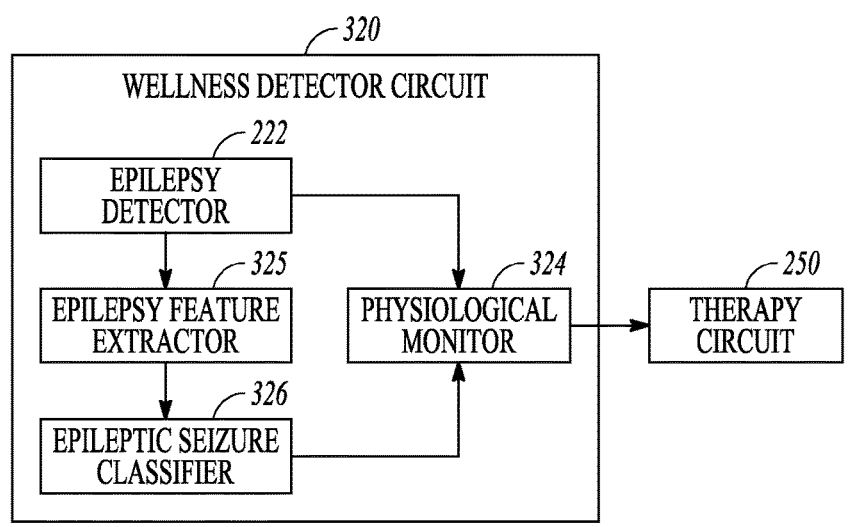
FIG. 3 illustrates generally an example of a portion of an epilepsy management system for classifying an epileptic seizure.

FIG. 3 illustrates generally an example of a portion of an epilepsy management system for classifying an epileptic seizure into different categories and managing the patient with the classified epileptic seizure. The categories of epilepsy may include two or more of a general seizure, a partial seizure, an absence seizure, a tonic seizure, a clonic seizure, and an atonic seizure, among others. Partial seizures, also known as "focal" or "local" seizures, begin in one location of the brain. Generalized seizures, which may begin everywhere in the brain at once, may be further classified into various types including absence seizures, tonic seizures, clonic seizures, tonic-clonic seizures, and atonic seizures. Absence seizures may begin suddenly but with a short duration of around 10-20 seconds, and typically do not accompanied by body or limb movement. A tonic seizure may be manifested as muscles in the chest, arms and legs contract and the back arches due to muscles stiffness, and loss of consciousness. As the chest muscles tighten, it becomes harder for the patient to breathe. A clonic seizure is typically accompanied by muscles and jerk. The elbows, legs and head will flex, and then relax rapidly at first, but the frequency of the spasms will gradually subside until they cease altogether. A tonic seizure is typically accompanied by a clonic seizure, which may be categorized as tonic-clonic seizures. Atonic seizures cause the muscles to go limp. The patient body may slump or crumple to the ground, possibly causing injury.

The wellness detector circuit 320 is an embodiment of the wellness detector circuit 220 of the multi-sensor epilepsy management system 200 as illustrated in FIG. 2. The wellness detector circuit 320 may be implemented as a dedicated or general purpose microprocessor circuit executing a set of instructions of performing the functions, methods, or techniques described herein. Alternatively, the wellness detector circuit 320 may include circuit sets comprising one or more other circuits or sub-circuits. As illustrated in FIG. 3, the wellness detector circuit 320 may include an epilepsy detector 222 to detect an epileptic event using the sensed physiological or functional signals, as previously discussed with reference to FIG. 2. The wellness detector circuit 320 may additionally include an epilepsy feature extractor 325 and an epileptic seizure classifier 326. Various types of epileptic seizures may have different duration, patient response patterns, or frequencies. The epilepsy feature extractor 325 may generate, based on the signal metrics of the sensed physiological or functional signals, one or more epileptic characteristics including an intensity, a duration, or a frequency of detected epileptic event. The epileptic seizure classifier 326 may classify the detected epileptic event into one of a plurality of epileptic seizure categories including a general seizure, a partial seizure, an absence seizure, a tonic seizure, a clonic seizure, and an atonic seizure, among others. The classification may be based on the epileptic characteristics such as intensity, duration, or frequency of detected epileptic event.

The wellness detector circuit 320 may include a physiological monitor 324 which may be an embodiment of the physiological monitor 224. The physiological monitor 324 is coupled to the epilepsy detector 222 and the epileptic seizure classifier 326, and may generate a wellness indicator indicating the impact of the detected epileptic event on patient health status and patient psychiatric health. The optional therapy circuit 250, coupled to the wellness detector circuit 320, may be configured to deliver the neural or cardiac electrostimulation therapy further in accordance with one or more epileptic characteristics or a classification of the epileptic event into one of a plurality of epileptic seizure types.

Figure 4:
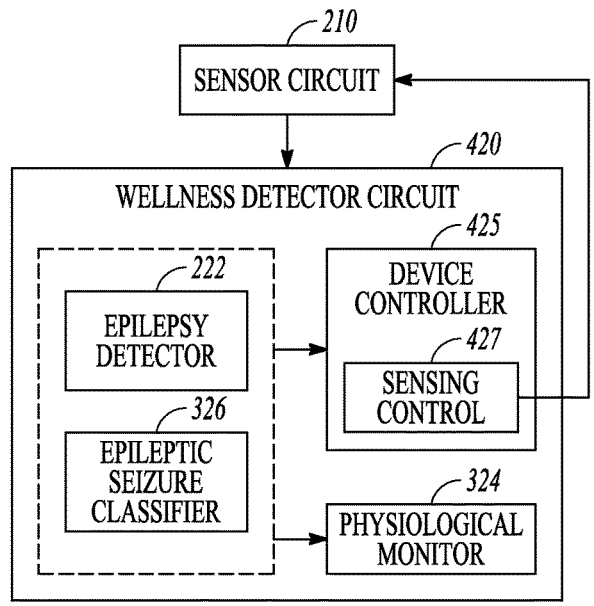
FIG. 4 illustrates generally an example of a portion of an epilepsy management system for controlling operation of the system based on the detected epileptic event.

FIG. 4 illustrates generally an example of a portion of an epilepsy management system for controlling system operation based on the detected epileptic event. The wellness detector circuit 420, which is an embodiment of the wellness detector circuit 220 or 320 as respectively illustrated in FIGS. 2-3, may include a device controller 425 configured to control the system operation, such as data acquisition by the physiological sensors, signal analysis, epilepsy detection, physiological monitoring, and data communication with the external system. The device controller 425 may be coupled to one or more of the epilepsy detector 222 and the epileptic seizure classifier 326. The device controller 425 may dynamically control the system behavior based on the epilepsy detection (e.g., a presence of an epileptic event), or additionally based on the classification of the epileptic seizure types as generated by the epileptic seizure classifier 326. In an example, the device controller 425 may include a sensing control 427 to control the sensor circuit 210 to sense and process the physiological or functional signals. In an example, in response to the detection of the epileptic event, the device controller 425 may control the sensor circuit 210 to operably change the data resolution, such as by increasing the sampling rate from a pre-epilepsy sampling rate to a peri-epilepsy sampling rate to sample a physiological or functional signal. The higher peri-epilepsy sampling rate may allow those signal metrics generated using the higher frequency signal components to be reliably extracted for epilepsy characterization or confirmation by an external processor. The sampling rate adjustment may be individually or independently controlled for different physiological or functional signals. Other data acquisition and processing parameters, such as time periods for data acquisition, amplification, signal filtering, or analog-to-digital conversion, may also be adjusted in response to epilepsy detection or the epileptic seizure classification. In an example, the device controller 425 may additionally or alternatively control the sensor circuit 210 to selectively activate or deactivate a sense channel, such as to initiate sensing of one physiological or functional signal, and/or terminate sensing of another physiological or functional signal.

Figure 5:
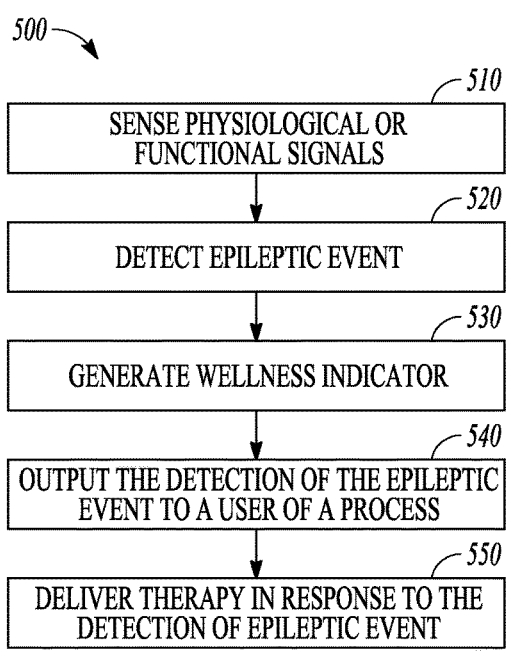
FIG. 5 illustrates generally an example of a method for detecting epilepsy in patient using an ambulatory device.

FIG. 5 illustrates generally an example of a method 500 for detecting epilepsy in a patient using an ambulatory device. The method 500 may be implemented and executed in an ambulatory medical device such as the IMD 112, or in a patient management system such as the external system 130. In an example, the method 500 may be implemented in and executed by the arrhythmia detection system 200 in FIG. 2.

The method 500 begins at 510 by sensing at least first and different second physiological or functional signals in a patient. The physiological or functional signals may be sensed using respective sensors such as the first and second sensors 202 and 204 as discussed with reference to the multi-sensor epilepsy management system 200 in FIG. 2. The physiological signals may include electrocardiograph (ECG), an electrogram (EGM), a heart rate signal, a heart rate variability signal, an intrathoracic impedance signal, an intracardiac impedance signal, an arterial blood pressure signal, a pulmonary artery pressure signal, a RV pressure signal, a LV coronary pressure signal, a blood pressure variability signal, a coronary blood temperature signal, a peripheral body temperature signal, a blood oxygen saturation signal, a heart sound (HS) signal, or a respiration signal (including, for example, respiration rate, tidal volume, minute ventilation, respiratory patterns), a galvanic skin response (GSR) signal, or a neural signal such as indicative of sympathetic or parasympathetic tone, among others. Examples of the functional signals may include a posture, a gait, a balance indicator, a locomotion pattern, a physical activity intensity or duration, or a grip strength signal, among others. Signal metrics may be generated from the physiological or functional signals. The signal metric represent physiological or functional changes in response to a patient disease progression, change in medication, change in health conditions, or change in posture or activity levels.

At 520, an epileptic event may be detected using the first and second physiological or functional signals. The signal metrics of the physiological or functional signals may be compared to one or more thresholds or to fit a computational model to determine the presence or absence of the epileptic event. For example, increases in heart rate, blood pressure, or respiratory rate, arrhythmias, or hypopnea and apnea may be evidence of an epileptic event. In an example, the epileptic event may be detected using a combination of signal metrics generated from the first and second physiological or functional signals. The signal metrics may be respectively weighted by weight factors when they are combined. The weight factors indicate respective physiological or functional signal reliability in evaluating a patient risk of developing an epileptic episode. Additionally or alternatively, the signal metrics may be combined using a computation model. A numerical risk score may be computed as weighted sum of individual scores representing likelihood of impending epilepsy predicted by individual signal metrics. An epileptic event is detected when the numerical risk score exceeds a specified risk threshold.

At 530, a wellness indicator may be generated upon a prediction or early detection of the epileptic seizure. The wellness indicator indicates an impact of epileptic seizure on the patient health. The physiological or functional signals may be trended over time during the detected epileptic event, or even extended after the termination of the epileptic event. The wellness indicator may be generated based on a trend of the physiological or functional signal over time during the detected epileptic event. In an example, the wellness indicator may include an epilepsy complication risk such as a risk of sudden unexpected death in epilepsy (SUDEP). In another example, the wellness indicator may include a detection of a patient risk of syncope, bradycardia or tachycardia, hypotension, or blood pressure instability. The identified risk may be used to identify patients that may benefit from a particular therapy or candidate for receiving a diagnostic or therapeutic device. In some examples, the wellness indicator may indicate an impact of the epilepsy on the functionality of an implantable device, such as arrhythmia detection or arrhythmia therapy, and provide an indication for therapy parameter adjustment, drug dosage titration, device reconfiguration, or device upgrade. The wellness indicator may include a risk of disordered breathing, or a risk of neurogenic pulmonary edema. In some examples, the wellness indicator may indicate a progression of an existing chronic disease.

At 540, the detection of the epileptic event may be output to a user or a process. In an example, a human-perceptible presentation of information, including the detection of the epileptic event or the wellness indicator, may be generated and displayed such as on the output unit 242 of a user interface 240 as illustrated in FIG. 2. In an example, alerts, alarms, emergency calls, or other forms of warnings may be generated to signal the presence or types of epileptic events, and the wellness indicator such as indicating deteriorated cardiac, hemodynamic, pulmonary, or neurological functions.

The method 500 may optionally include a step 550 for delivering a therapy to the patient in response to the detection of an epileptic event. Examples of the therapy may include electrostimulation therapy delivered to a neural target to treat epileptic seizure, such as SCS, DBS, or VNS. The therapy may additionally or alternatively include drug therapy such as delivery of antiepileptic medications through a drug infusion pump device. In an example, the therapy may be delivered in a closed-loop fashion. In some examples, peri- and post-epileptic assistive therapy may be a delivered at 550 to maintain adequate cardiorespiratory support during and after epilepsy treatment. The assistive therapy may be sustained until a patient physiologic response adequately recovers, such as to a level comparable to pre-epileptic baseline.

Figure 6:
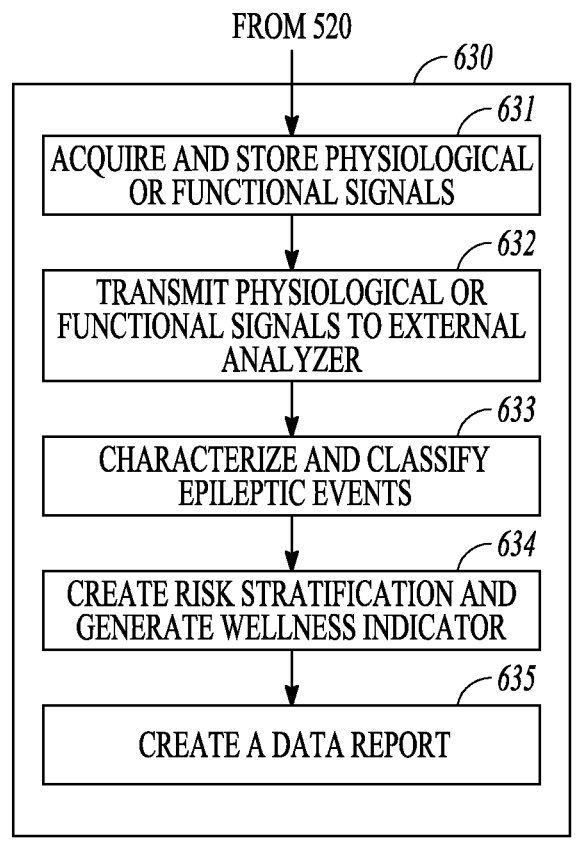
FIG. 6 illustrates generally an example of a method for generating a wellness indicator with the use of an external device.

FIG. 6 illustrates generally an example of a method 630 for generating a wellness indicator with the use of an external device. The method 630 may be an embodiment of the step 530 of the method 500. In an example, the method 630 may be implemented in and executed by the arrhythmia detection system 200 in FIG. 2.

At 631, upon the detection of an epileptic event, the physiological or functional signals may be acquired and stored in a memory, such as the memory 230 of multi-sensor epilepsy management system 200. Physiological or functional signals may be sensed at 631 at an adjustable data resolution different than the data resolution used for signal sensing at 510 for epileptic event detection. In an example, a higher peri-epilepsy sampling rate may be used at 631 to sample a physiological or functional signal. The higher peri-epilepsy data resolution may allow those signal metrics based on higher frequency signal components to be reliably extracted for subsequent epilepsy characterization, classification, and confirmation by an external device. The sampling rate adjustment may be individually or independently controlled for different physiological or functional signals. Storage of the sensed physiological or functional signals may be continuous, periodic, or triggered by a user command or a specified event. In an example, a detection of epileptic event at 520 may trigger the data storage of selected physiological or functional signals with respectively specified time duration. For example, the stored data may sustain from a specified pre-event time prior to the onset of the epilepsy detection till a specified post-event time after the termination of the epileptic event.

At 632, the physiological or functional data may be transmitted to an external device such as included in the external system 130. Other device data, such as sensing, pacing, timestamps, or event markers as generated and stored in an implantable cardiac device, may also be transmitted. An interrogating device, such as an AMD programmer, a remote server-based patient management system, or a standard personal computer defined predominantly by physiological analysis and medical diagnosis software, may request access to the stored sensor signals and the results of epileptic event detection stored in the memory 230. Upon request, the requested information may be transmitted to the interrogating device such as via the communication link 120. The data may be transmitted in a batch mode, in a specified transmission cycle such as every one hour, to save the power consumption and efficiently use the communication bandwidth.

At 633, the detected epileptic events may further be characterized, and classified into one of a number of different epileptic seizure types, such as by the epileptic seizure classifier 326 as illustrated in FIG. 3. The categories of epilepsy may include two or more of a general seizure, a partial seizure, an absence seizure, a tonic seizure, a clonic seizure, and an atonic seizure, among others. One or more epileptic characteristics including intensity, duration, or a frequency of detected epileptic event may be generated from the physiological or functional signals. The detected epileptic event into one of a plurality of epileptic seizure categories based on the epileptic characteristics such as intensity, duration, or a frequency of detected epileptic event. In an example, retrospective data analysis based on computationally intensive algorithms, such as machine-learning algorithms, may be performed at the external device. The analysis may incorporate characterization and epileptic event classification. Based on the analysis, the detection of the epileptic event at 520 may be confirmed or rejected.

At 634, risk stratification may be performed to identify patient at elevated risk of developing an impending epileptic event. The stratification may be based on characterization and classification of epileptic events provided at 633. A wellness indicator may be generated to indicate the impact of the detected epileptic event on patient health status. An individualized prediction of an impending epileptic event may be made based on the wellness indicator, such as to allow the patient to have enough time to react.

At 635, a data report may be created, and provided to a healthcare provider to assist diagnosis and treatment of epilepsy. The data report may include summaries of the physiological or functional data, trends of signal metrics, characterization of the epileptic event such as number of epileptic events, histogram or other measures of statistical distribution of epileptic event duration, or classification of the detected epileptic event, among others. The report may be in electronic format such as be display on the screen and electronically transmitted, or alternatively be a printed copy such as a data strip with textual or graphical presentation of the data. The epileptic event may be highlighted or otherwise accentuated or identified to facilitate interpretation, analysis, or adjudication by the healthcare provider. In some examples, the report may include information about the effects of epileptic events on an existing device therapy, or impact on the progression of existing chronic diseases. In some examples, the report may include recommendations for therapy parameter adjustment, drug dosage titration, device reconfiguration, or device upgrade.

Figure 7:
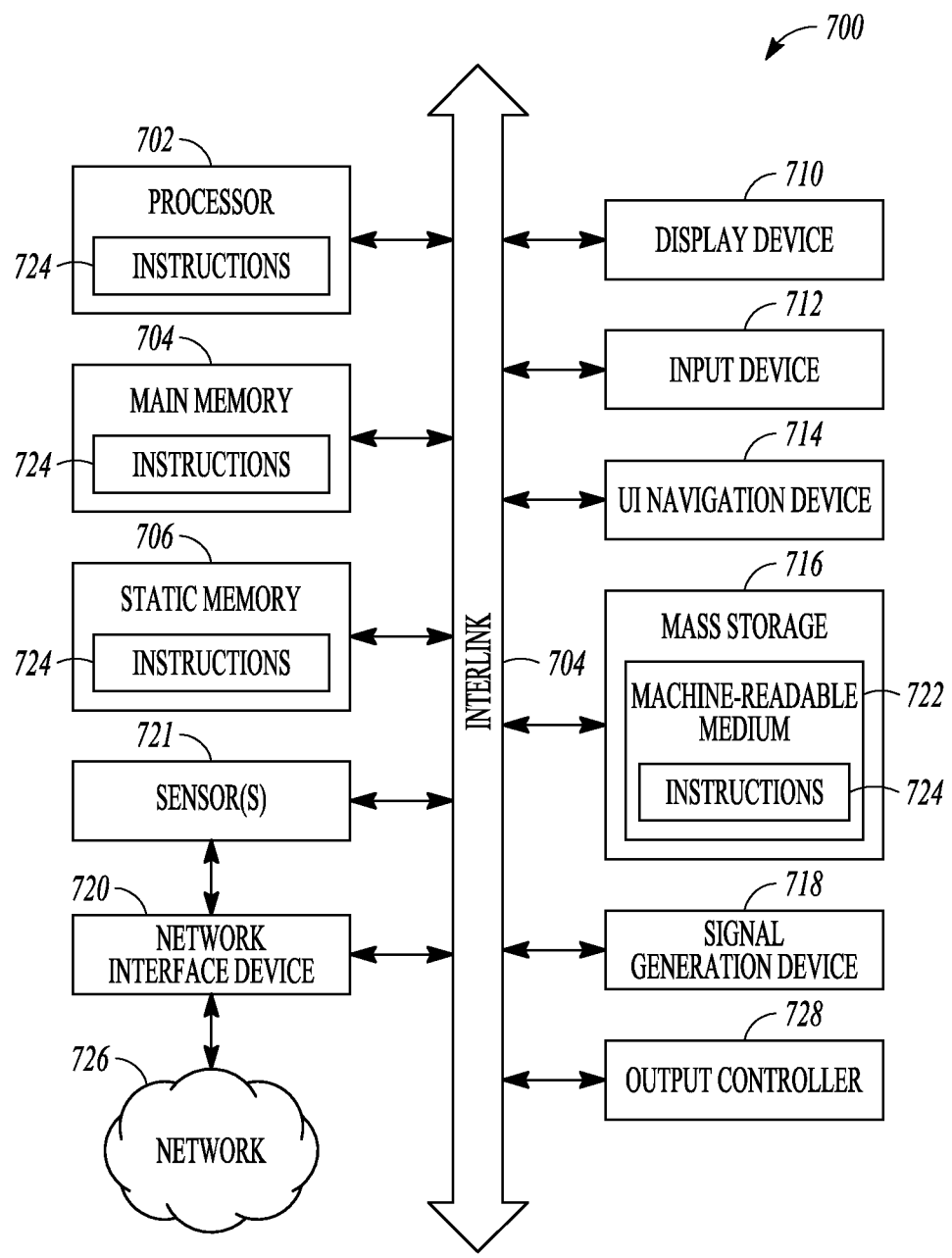
FIG. 7 illustrates generally a block diagram of an example machine upon which any one or more of the techniques (e.g., methodologies) discussed herein may perform.

FIG. 7 illustrates generally a block diagram of an example machine 700 upon which any one or more of the techniques (e.g., methodologies) discussed herein may perform. Portions of this description may apply to the computing framework of various portions of the LCP device, the IMD, or the external programmer.

In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710 (e.g., a raster display, vector display, holographic display, etc.), an alphanumeric input device 712 (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensor. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 716 may include a machine readable medium 722 on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine readable media.

While the machine readable medium 722 is illustrated as a single medium, the term "machine readable medium" may include a single medium or multiple media (e.g., a centralized or distributed database, and/or associated caches and servers) configured to store the one or more instructions 724.

The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 724 may further be transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for monitoring a patient at risk of epilepsy, the system comprising:
   a sensor circuit configured to receive physiological information including heart sound information of the patient;
   a wellness detector circuit communicatively coupled to the sensor circuit, the wellness detector circuit configured to:
   detect an epileptic event using at least the received heart sound information; and
   generate a wellness indicator based on a trend of the received physiological information over time during the detected epileptic event, the wellness indicator indicating an impact of the detected epileptic event on the health status of the patient; and
   an output unit configured to output the detection of the epileptic event or the wellness indicator to a user or a process.

2. The system of claim 1, comprising a memory configured to store the received physiological information in response to the detection of the epileptic event.

3. The method system of claim 1, wherein the wellness indicator includes one or more of:
   a risk of sudden unexpected death in epilepsy;
   a degree of progression of a chronic disease;
   a risk of cardiac arrhythmia;
   a risk of a syncope;
   a risk of pulmonary edema; or
   a risk of disordered breathing pattern.

4. The system of claim 1, wherein the received physiological information further includes one or more of:
   a heart rate signal;
   a heart rate variability signal;
   a respiration rate signal;
   a blood pressure signal;
   a blood pressure variability signal; or
   a peripheral body temperature signal.

5. The system of claim 1, wherein the sensor circuit is configured to receive functional information of the patient including one or more of:
   a posture;
   a physical activity intensity or duration;
   a grip strength signal;
   a gait; or
   a balance indicator; and
   wherein the wellness detector circuit is configured to detect an epileptic event further using the received functional information.

6. The system of claim 5, wherein the wellness detector circuit is configured to detect the epileptic event using the physiological information and the functional information each weighted by weight factors indicating respective physiological or functional information reliability in evaluating a patient risk of developing an epileptic episode.

7. The system of claim 1, wherein the wellness detector circuit is further configured to:
   generate, from the sensed first and second physiological or functional signals, one or more epileptic characteristics including an intensity, a duration, or a frequency of detected epileptic event; and
   classify the detected epileptic event into one of a plurality of epilepsy types using the one or more epileptic characteristics.

8. The system of claim 1, wherein the sensor circuit is configured to acquire the physiological information at a peri-epilepsy sampling rate higher than a pre-epilepsy sampling rate in response to the detection of the epileptic event.

9. The system of claim 1, comprising an ambulatory medical device (AMD) communicatively coupled to the first and second sensors, the AMD including at least a portion of one or more of the sensor circuit, the wellness detector circuit, and the output unit.

10. The system of claim 9, further comprising an external system in communication with the AMD, the external system including an external data processor configured to confirm the detection of the epileptic event.

11. The system of claim 1, further comprising a therapy unit configured to deliver a neural or cardiac electrostimulation therapy in response to the detection of an epileptic event.

12. The system of claim 11, wherein the therapy unit is configured to deliver the neural or cardiac electrostimulation therapy further in accordance with one or more epileptic characteristics or a classification of the epileptic event into one of a plurality of epileptic seizure types.

13. A method for detecting epilepsy in a patient with an ambulatory device, the method comprising:
receiving, via the ambulatory device, physiological information including heart sound information of the patient;
detecting an epileptic event using at least the received heart sound information;
generating a wellness indicator based on a trend of the received physiological over time during the detected epileptic event, the wellness indicator indicating an impact of the detected epileptic event on the health status of the patient; and
outputting the detection of the epileptic event or the wellness indicator to a user or a process.

14. The method of claim 13, wherein the wellness indicator includes one or more of:
a degree of progression of a chronic disease;
a risk of sudden unexpected death in epilepsy;
a risk of cardiac arrhythmia;
a risk of a syncope;
a risk of pulmonary edema; or
a risk of disordered breathing pattern.

15. The method of claim 13, further comprising receiving functional information of the patient, wherein detecting the epileptic event includes linearly or nonlinearly combining the physiological information and the functional information each weighted by weight factors indicating respective physiological or functional information reliability in evaluating a patient risk of developing an epileptic episode.

16. The method of claim 13, further comprising:
generating, from the sensed first and second physiological or functional signals, one or more epileptic characteristics including an intensity, a duration, or a frequency of detected epileptic event; and
classifying the detected epileptic event into one of a plurality of epilepsy types using the one or more epileptic characteristics.

17. The method of claim 13, wherein sensing the first and second physiological or functional signal includes acquiring the physiological information at a peri-epilepsy sampling rate higher than a pre-epilepsy sampling rate in response to the detection of the epileptic event.

18. The method of claim 13, further comprising delivering a neural or cardiac electrostimulation therapy in response to the detection of an epileptic event.

19. The method of claim 18, wherein the neural or cardiac electrostimulation therapy is delivered further in accordance with one or more epileptic characteristics or a classification of the epileptic event into one of a plurality of epileptic seizure types.

20. An implantable medical device, comprising:
a sensor circuit configured to sense physiological information including heart sound information of the patient; and
a processor circuit configured to:
detect an epileptic event using at least the sensed heart sound information; and
generate a wellness indicator based on a trend of the sensed physiological information over time during the detected epileptic event, the wellness indicator indicating an impact of the detected epileptic event on the health status of the patient.

* * * * *